United States Patent [19]

Chang et al.

[11] Patent Number: 5,270,169

[45] Date of Patent: Dec. 14, 1993

[54] DETECTION OF HLA ANTIGEN-CONTAINING IMMUNE COMPLEXES

[75] Inventors: Chin-Hai Chang, Los Altos; Philippe Pouletty, Atherton, both of Calif.

[73] Assignee: SangStat Medical Corporation, Menlo Park, Calif.

[21] Appl. No.: 902,971

[22] Filed: Jun. 23, 1992

[51] Int. Cl.$^5$ .................. G01N 33/537; G01N 33/564; G01N 33/577

[52] U.S. Cl. .................... 435/7.24; 435/7.21; 435/7.92; 435/7.94; 435/7.95; 435/969; 435/975; 436/507; 436/538; 436/541; 436/548

[58] Field of Search ............. 435/7.21, 7.24, 7.92, 435/7.94, 969, 975, 7.95; 436/506, 507, 538, 541, 548

[56] References Cited

U.S. PATENT DOCUMENTS

| | | | |
|---|---|---|---|
| 4,143,124 | 3/1979 | Masson et al. | 435/7.92 |
| 4,810,632 | 3/1989 | McMillan | 436/507 X |
| 4,925,788 | 5/1990 | Liberti | 436/507 X |

OTHER PUBLICATIONS

H. FF. S. Davies et al, *Transplantation*, 47, 524–527, 1989.
A. Ferreira et al, *Journ. Immunol. Meth.*, 65, 373–381, 1983.
Martin, et al. (1987) Transplantation 44:50–53. Post-transplant antidonor lymphocytotoxic anibody production in relation to graft outcome.
Duqesnoy, et al. (1990) Transplantation 50:427–437. Multiscreen serum analysis of highly sensitized renal dialysis patients for antibodies toward public and private class I HLA determinants.
Grosse-Wilde, et al. (1989) J. Immunogenetics 16:149–155. Allotyping for HLA class I using plasma as antigen source.
Doxiadis and Grosse-Wilde (1989) Vox Sang 56:196–199. Typing for class I gene products using plasma as a source.
Tsuji, et al. (1985) Tokai J. Clin. Exp. Medicine 10:169–174. Biological significance of serum soluble HLA–class I antigens in bone marrow transplantation.
Stevenson, et al. (1986) J. Immunol. Methods 86:187–190. Analysis of soluble HLA class II antigenic material in patients with immunological diseases using monoclonal antibodies.
Fauchet, et al. (1989) Transplantation 30:114–129. Occurence and specificity of anti-B lymphocyte antibodies in renal allograft recipients.
Talbot, et al. (1988) J. Immunol. Methods 112:279–283, Rapid detection of low levels of donor specific IgG by flow cytometry with single and dual colour fluorescence in renal transplantation.
Iwaki, et al. (1988) Clin. Transplantation 2:81–84. Successful transplants across T warm–positive crossmatches due to IgM antibodies.
Lee and Taguchi (1989) Archives of Virology 108:247–257. Rapid identification and typing of herpes simplex virus by a new enzyme immunoassay with peroxidase-labeled complement Clq.

*Primary Examiner*—David Saunders
*Attorney, Agent, or Firm*—Bertram I. Rowland

[57] ABSTRACT

The invention provides for methods and compositions to detect the presence of anti-HLA antibodies, HLA antigen or preformed HLA-containing immune complexes in biological samples. The complement protein Clq is bound to a solid substrate, then mixed with a biological sample containing immune complexes. The immune complexes are preformed, or formed by adding HLA antigens to a biological sample containing antibodies to HLA, or alternatively, by combining a biological sample containing HLA antigens with defined antibodies to HLA. The immune complexes bind to Clq, and are then detected by the addition of a labeled reagent.

17 Claims, No Drawings

DETECTION OF HLA ANTIGEN-CONTAINING IMMUNE COMPLEXES

INTRODUCTION

Technical Field

The field of this invention is the detection of HLA antigens and antibodies to HLA antigens in biological samples.

BACKGROUND

In many transplantation type situations, there is concern for differences between the allotype, especially the HLA type, of a cell source and the cell recipient. In situations where allogeneic cells or tissue are taken from a donor and introduced into a recipient, it is desirable that the donor and recipient be as closely HLA matched as possible. The presence in the patient serum of antibodies against HLA antigens of the donor (donor specific crossmatch) or against a high percentage of HLA alleles (PRA testing) predicts a high risk of graft rejection.

The determination of HLA phenotype (H typing) is useful in numerous situations such as transplantation, platelet transfusion and forensic or paternity testing. The standard technique for HLA typing and detection of anti-HLA antibodies is microlymphotoxicity, where serum containing antibodies is incubated with HLA antigen-expressing lymphocytes, then with complement. The level of cytotoxicity is then estimated by discriminating between dead and viable cells using various dyes. This method has numerous disadvantages: it is labor intensive, time consuming, requires isolation of cells, requires viable cells, is nonspecific for HLA, and requires a subjective evaluation. Flow cytometry may also be used but requires a large number of cells and expensive instrumentation.

It is therefore of interest to provide alternative techniques which can be performed simply, can be automated, do not share the shortcomings described above, provide a readily discernible result which is significant for the prognosis of graft acceptance, and comparable to data from existing tests.

RELEVANT LITERATURE

References of interest include Duquesnoy et al. (1990) Transplantation 50: 427-37; Martin et al. (1987) Transplantation 44: 50-53; Grosse-Wilde et al. (1989) J. Immunogenet. 16: 149-55; Doxiadis and Grosse-Wilde (1989) Vox Sang 56: 196-99; Davies et al. (1989) Transplantation 47: 524-27; Tsujiet et al. (1985) Tokai J. Exp. Clin. Med. 10: 169-74; Stevenson et al. (1986) J. Immunol. Methods 86: 187-90; Fauchet et al. (1989) Transplantation 30: 114-129; Talbot et al. (1988) J. Immunol. Methods 112: 279-83; Iwaki et al. (1988) Clin. Transplantation 2: 81-84.

SUMMARY OF THE INVENTION

Methods and compositions are provided for detecting the presence of anti-HLA antibodies, HLA antigen or complexes of HLA antigens and antibodies in biological samples. In the absence of preformed complexes a reagent is added to the biological sample resulting in immune complexes, depending upon the presence of complementary members to the reagent in the sample. The complement protein Clq bound to a solid substrate is then combined with the biological sample for a determination whether the sample contains immune complexes comprising HLA antigen.

The immune complexes are formed by adding defined HLA antigens to a biological sample containing antibodies to HLA, or by combining a biological sample containing HLA antigens with defined antibodies to HLA. In some instances, following transplantation, the complexes will be preformed, by graft originated HLA antigens and recipient anti-HLA antibodies. Immune complexes bind to the immobilized Clq protein, and are then detected by any convenient means.

DESCRIPTION OF THE SPECIFIC EMBODIMENTS

A simple, rapid and accurate method is provided for the determination of the presence of at least one particular HLA allele, and/or the presence of antibodies to at least one HLA allele and/or preformed immune complexes consisting of at least one HLA allele and antibody. The method employs complement protein Clq bound to a solid substrate or surface. In the absence of preformed complexes, a biological sample is mixed with either HLA antigen or anti-HLA antibody of interest, and then added to the immobilized Clq protein.

If there is a reaction between the antigen or antibody of interest and a component of the biological sample, normally a soluble protein component, then immune complexes will be formed. Immune complexes will specifically bind to the Clq protein, without substantial interfering background.

The presence of components in the sample which have formed immune complexes is determined by detecting the presence of immune complexes bound to the surface. In a preferred embodiment, where one is primarily interested in detecting either Class I HLA antigens, or antibodies to Class I HLA antigens, the immune complexes may be detected by antibody to $\beta 2$-microglobulin, which is an invariant chain of Class I antigens.

Embodiments of this invention find use in identifying antibodies to transplant donor histocompatibility antigens (crossmatching), identifying histocompatibility antigens with antibodies of known specificities (HLA typing), identifying general alloreactivity toward a panel of histocompatibility antigens (Panel Reactive Antibody testing, PRA), antibody screening and monitoring immune complex formation in post-graft situations.

HLA antigens refers to gene products of the major histocompatability complex (MHC) locus. The antigens may be Class I, Class II, or other alleles associated with the MHG locus.

Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. Preferred samples are physiological fluids such as blood or derivatives thereof, such as serum or plasma (hereafter "blood"), with or without specimen pretreatment such as dilution.

Purified Clq protein from a number of species is commercially available or may be readily obtained. It may be bound to the support in accordance with known techniques, depending on the nature of the support. Binding may be covalent or non-covalent.

The support may be any convenient solid support, which may include container walls or bottoms, e.g.

microtiter plate wells, test tubes. macro, or micro-beads, slides, absorbent films, porous matrices, membranes, particles, e.g. magnetic particles, or the like. The particular support is not critical, and any support may be used, where non-specific binding may be minimized, where the support does not significantly interfere with the measurement, and where the support allows for a convenient protocol. A large number of solid supports are known, which are activated, and will form covalent bonds with proteins. Other supports are known, where the support may be activated by adding reagents, resulting in reaction with proteins. In addition, in some instances, incubating under low temperature, ambient temperature or mild heating will provide for non-covalent binding of proteins to the support. The support may include glass, plastics, e.g. polystyrene, polyacrylate, polyethylene, polypropylene, latex, etc., cellulose, e.g. paper, nitrocellulose, cellulose acetate, glass fibers, and the like.

In preparing the Clq bound support, a blocking group may be added, conveniently an innocuous protein or amino acid derivatives for reacting with free active sites, or a detergent, so as to reduce non-specific binding. Numerous blocking materials have been employed, such as milk, bovine serum albumin, casein, gelatin, SDS, ethanolamine, $\beta$-globin, Tween 20, etc.

Once the solid support has been prepared, the specimen and the immunoglobulin or antigen reagent may be combined. The specimen may have been subject to prior treatment, such as dilution, removal of interfering materials, e.g. red blood cells, background generating factors, coagulating agents, and the like. The specimen, which will generally be from about 1 ul to 0.5 ml, may then be combined with the reagent.

In one embodiment the sample will be analyzed for the presence of HLA antigen(s). A reagent solution of one or more monoclonal antibodies, or alloantisera, usually having known specificity against HLA antigen(s), although the HLA specificity of alloantisera need not be known, will be added to the biological sample in order to detect the presence of, or type, the antigen. The antibody reagent employed to form immune complexes may include monoclonal antibodies and/or alloantisera, neat, diluted or affinity purified antisera, which may be specific for one or more allelic products of interest.

In another embodiment, a reagent solution comprising HLA antigen of known source or allotype will be added to the biological sample in order to detect the presence of specific antibodies. The soluble HLA antigen may be derived from supernatants of lymphoblastoid cell lines of known HLA type, which are cultured with or without stimulating agents such as cytokines or mitogens. The HLA antigen may also be extracted from cells or tissues using enzymatic digestion or detergent solubilization; or derived from biological fluids such as blood, serum, plasma, dialysis fluid and the like; or derived from the gene product of a cloned HLA gene in an expression system; or a synthetic HLA antigen may be used which mimics the antigenic reactivity of HLA epitopes. The amount of antigen used will usually be from about 0.01 ng to 10 $\mu$g/test, and more usually from about 2 ng to 100 ng/test.

The specimen and reagent will form immune complexes when both members of a reciprocal binding pair are present, i.e. a specific antigen and complementary antibody. Some of the immune complexes, depending on valency and isotype of the antibodies, are then able to bind to the Clq protein immobilized on the support.

The reciprocal reagents, when needed, will normally be combined prior to combining with the solid support, although the specimen, reagent and solid support may be combined simultaneously or the specimen may be first added to the solid support, or the antibody may be added first, depending upon the protocol and what is being measured. The assay medium will usually (but not necessarily) be buffered with an appropriate buffer, at a pH in the range of about 4-10. The buffer may be phosphate, carbonate, Hepes, Mops, Tris, borate, citrate, or the like. Generally, the buffer concentration will be sufficient to maintain the desired pH, usually being at least 10 mM and not more than about 500 mM. Other additives may be present in minor amounts, such as innocuous proteins, generally not exceeding about 25%, stabilizing agents, e.g. azide, etc.

The mixture may be incubated for sufficient time for reaction to occur at each stage. Usually, incubation times range from about 1 min. to 12 hours, more usually from about 5 min. to 30 min., except when a flow-through device is used where the time may be shorter. After sufficient time for binding to the support, the support may be washed by any convenient means, using water or a buffered medium, generally at a pH in the range of about 4-10 and having from about 10-500 mM of a buffering agent, with or without detergents or proteins. One or more washes may be employed to ensure substantial removal of non-specific binding, usually a plurality of washes where binding of the complexes to the surface is found to be maintained.

After the incubation and washings, the presence of HLA antigen bound to the surface may be determined. While any convenient, accurate method maybe employed for the detection of the surface bound complexes, there will be preferred methodologies. Methodologies employing binding moieties such as antibodies, polyclonal sera, monoclonal antibodies or fragments thereof, peptides, or viral proteins which will bind to the HLA antigen or other convenient marker may be used. For the HLA antigens, the antibodies or other binding moieties may be directed to conserved or polymorphic regions of one or both of the chains of the HLA Class I or Class II antigen. By employing directly or indirectly labelled antibodies or other binding moieties, where the label allows for detection, the presence of the immune complexes may be determined.

In one protocol, a reduction in the amount of binding of immune complexes to Clq protein may be detected by the use of a competition assay. A defined amount of Clq protein and a known amount of labeled immune complexes are added to the sample and reagent mix. A reduction in the amount of binding of labeled complex to the surface will be related to the presence in the sample of the immune complex.

The antibody or other ligands for detection, particularly anti-HLA antibody, may be labeled, so as to be directly detectable. Labels may include dyes, fluorescers, enzymes, chemiluminescers, particles, radioisotopes, biotin to bind to labeled avidin, or other directly or indirectly detectable agent. With the enzymes, various substrates may be employed, which provide for light absorption, fluorescence, chemiluminescence, or the like. The particular label is not critical to this invention and is primarily a matter of convenience and sensitivity. In the case of an enzyme label, the reaction will usually be timed and terminated in accordance with any convenient means for the determination.

When convenient, a negative control assay will be carried out for better accuracy or reproducibility, where the specimen will be replaced with buffer or buffer containing innocuous antibodies or other medium which mimics the nature of the specimen, e.g. a nutrient medium, cell culture supernatant, etc. or a known negative specimen. Thus, the control test will generally mimic, as closely as possible, the specimen assay.

Various protocols other than the protocols described above may be employed, depending upon the materials and devices employed and available.

The reagents for the subject invention can be provided in a kit. The kit would include the Clq protein bound to the support, control solutions, and the reagents necessary for the determination, which as already indicated, could be reagents for an enzyme immunoassay, radioimmunoassay, fluorescence immunoassay, flow cytometric assay, or chemiluminescent immunoassay. Other reagents which may be present include buffer, which may be appropriately diluted, substrates, in the case of an enzyme immunoassay, stop solution to stop color development and software program to record and/or analyze the results and the allele specificities. The results may be determined in accordance with the nature of the assay, using a spectrophotometer, fluorimeter, scintillation counter, reflectometer, luminometer, flow cytometer, gamma-counter, laser, etc.

The subject method has numerous advantages. The conventional microlymphocytotoxicity assay is based on complement-mediated cell lysis. The binding of Clq protein is the first event in activating the complement cascade. The subject method utilizes the binding properties of Clq in a novel way, that allows for a good correlation between this test, and the microlymphocytotoxicity assay. The method is also able to use alloantisera, it permits rapid typing of numerous alleles or detection of anti-HLA antibodies, allows quantitative objective reading of results, has a simple protocol and can employ a wide variety of reagents, which are readily available.

The following examples are offered by way of illustration and not by way of limitation.

EXPERIMENTAL

A 1 mg/ml stock solution of Clq protein (Immunicon or Sigma) was diluted to 20 ug/ml in 10 mM $NaHCO_3$, pH 9.5. and was immediately dispensed to the microtiter plates (Nunc) at 100 ul/well. The plates were capped with parafilm and left at room temperature overnight on a flat surface. The plates were then washed 5 times with 10 mM Tris-HCl, pH 7.3, and then coated with 0.2% casein-TBS, pH 7.2, for 2-3 hours at room temperature to block the vacant sites. The plates were further washed with 10 mM Tris-HCl, pH 7.3 for 3 more times, and then promptly used in the assay.

For plate controls, the following two tubes were set up for each plate:
(a) 10 ul PBS+75 ul RPMI
(b) 10 ul PBS+75 ul 7666Ag (the culture supernatant of a lymphoblastoid cell line which is a source of soluble HLA antigen)

For each serum specimen a reaction tube was set up containing:
(c) 10 ul serum+75 ul 7666Ag In some experiments an RPMI control was also set up for each serum specimen to determine the sample background, as follows:
(d) 10 ul serum+75 ul RPMI The above tubes were incubated at 37° for 1 hour. Then 150 ul PBS was added to each tube, to reach a final volume of 235 ul.

In each experiment several normal male sera, which were presumed to be negative for anti-HLA antibodies, were run simultaneously with a panel of alloantisera that contained certain anti-HLA antibody.

100 ul of the mixture in each tube was transferred to the microtiter plate well in duplicate. The plate was incubated at 37° for 90 minutes.

The plates were washed 5 times with 0.2% casein-TBS. 100 ul of properly diluted (about 1:1600) horseradish peroxidase-rabbit anti-human $\beta$2-microglobulin was added to each well, and the plates were incubated for one hour at room temperature. The plates were then washed another 5 times with 0.2% casein-TBS. To each well was then added 100 ul of OPD substrate solution (3 mg/ml) and the medium incubated at room temperature for 30 minutes. The reaction was stopped by adding 100 ul of 1 N HCI to each well. The optical density was read at 490 nm with an ELISA plate reader.

ANALYSIS OF DATA

The data was analyzed by averaging the duplicate readings for each sample, both the plate and sample negative controls (a) and (d), and the experimental tube (c). Two ratios were calculated, Ratio A. the signal (c) to plate background (a)
Ratio B. the signal (c) to sample background (d)

The level of background signal was determined to be Ratio A and/or Ratio B for normal male serum+2 standard deviations.

Table 1 gives results for one experiment. Ratio A+2 standard deviations for normal male serum was determined to be 1.94, therefore, in order to be positive a sample had to have a value greater than 2.29 for Ratio A or 1.94 for Ratio B.

TABLE 1

| SAMPLE | MEAN OD | BACK-GROUND | RATIO A | RATIO B | ASSAY RESULT | MICRO-LYMPHO-CYTO-TOXICITY |
|---|---|---|---|---|---|---|
| sample 1 | .144 | .067 | 2.44 | 2.16 | Positive | Positive |
| sample 2 | .282 | .073 | 4.77 | 3.88 | Positive | Positive |
| sample 3 | .140 | .069 | 2.37 | 2.02 | Positive | Positive |
| sample 4 | .176 | .067 | 2.98 | 2.64 | Positive | Positive |
| sample 5 | .172 | .068 | 2.91 | 2.55 | Positive | Positive |
| sample 6 | .211 | .066 | 3.57 | 3.19 | Positive | Positive |
| sample 7 | .154 | .067 | 2.61 | 2.32 | Positive | Positive |
| sample 8 | .423 | .062 | 7.17 | 6.82 | Positive | Positive |
| sample 9 | .125 | .065 | 2.11 | 1.93 | Negative | Positive |
| sample 10 | .146 | .072 | 2.47 | 2.04 | Positive | Positive |
| sample 11 | .110 | .062 | 1.85 | 1.76 | Negative | Positive |

TABLE 1-continued

| SAMPLE | MEAN OD | BACK-GROUND | RATIO A | RATIO B | ASSAY RESULT | MICRO-LYMPHO-CYTO-TOXICITY |
|---|---|---|---|---|---|---|
| sample 12 | .400 | .067 | 6.77 | 5.96 | Positive | Positive |
| sample 13 | .176 | .068 | 2.97 | 2.6 | Positive | Positive |
| sample 14 | .754 | .068 | 12.77 | 11.01 | Positive | Positive |
| sample 15 | .609 | .077 | 10.3 | 7.9 | Positive | Positive |
| sample 16 | .109 | .069 | 1.84 | 1.57 | Negative | Positive |
| sample 17 | .126 | .070 | 2.12 | 1.81 | Negative | Positive |
| sample 18 | 1.499 | .074 | 25.4 | 20.4 | Positive | Positive |
| sample 19 | .164 | .068 | 2.77 | 2.40 | Positive | Positive |
| sample 20 | .144 | .072 | 2.43 | 2.00 | Positive | Positive |
| sample 21 | 1.56 | .068 | 2.63 | 2.28 | Positive | Positive |
| sample 22 | .178 | .069 | 3.01 | 2.58 | Positive | Positive |
| sample 23 | .155 | .064 | 2.63 | 2.42 | Positive | Positive |
| sample 24 | .678 | .070 | 11.48 | 10.04 | Positive | Positive |
| sample 25 | .236 | .072 | 3.99 | 3.29 | Positive | Positive |
| sample 26 | .307 | .069 | 5.2 | 4.48 | Positive | Positive |
| sample 27 | .897 | .063 | 15.2 | 14.2 | Positive | Positive |
| sample 28 | 1.448 | .066 | 24.5 | 21.9 | Positive | Positive |
| sample 29 | .135 | .065 | 2.28 | 2.07 | Positive | Positive |
| sample 30 | .276 | .066 | 4.67 | 4.17 | Positive | Positive |
| sample 31 | .706 | .066 | 11.96 | 10.77 | Positive | Positive |

What is claimed is:

1. A method for detecting the presence of an analyte comprising at least one HLA antigen and/or antibody to at least one HLA antigen in a human biological specimen, said method comprising:
combining said biological specimen with (1) reciprocal reagent to said analyte, wherein said reciprocal reagent to said analyte is a monoclonal antibody or allotypic antiserum to said analyte when said analyte is an HLA antigen and is an HLA antigen when said analyte is said antibody, with the proviso that when said sample is being tested for preformed immune complexes of said analyte said reagent need not be added, and (2) Clq bound to a solid support; and
detecting the presence of immune complexes present on said support using a directly or indirectly labelled anti-HLA binding moiety wherein said label is capable of providing a detectable signal,
wherein a difference in signal from said specimen as compared to a signal from a reference value is indicative of the presence of said analyte.

2. A method according to claim 1, wherein said analyte is an HLA antigen, said reciprocal reagent is monoclonal antibody or allotypic antiserum to said HLA antigen, and said detecting comprises:
washing said solid support substantially free of non-specifically bound HLA antigen;
adding a labeled binding moiety capable of binding to said HLA antigen; and
detecting the presence of said labeled binding moiety bound to said support.

3. A method according to claim 2, wherein said labeled binding moiety is an antibody directed against a component of the HLA antigen.

4. A method according to claim 2, wherein said HLA antigen is a Class I HLA antigen and said labeled binding moiety is an antibody directed against β-2 microglobulin.

5. A method according to claim 2, wherein said labeled binding moiety is enzyme labeled antibody directed against an HLA antigen.

6. A method according to claim 2, wherein said labeled binding moiety is a fluorochrome labeled antibody directed against an HLA antigen.

7. A method for detecting the presence of at least one Class I HLA antigen in a biological specimen, said method comprising:
combining said biological specimen with :(1) monoclonal antibody or allotypic anti-serum to said at least one Class I HLA antigen; and (2) Clq bound to a solid support;
washing said solid support substantially free of non-specifically bound HLA antigen;
adding a labeled binding moiety comprising antibody directed against β-2 microglobulin; and
detecting by means of a labelled binding moiety the presence of immune complexes present on said support as compared to a reference value,
wherein a difference in signal from said specimen as compared to said reference value is indicative of the presence of said Class I HLA antigen.

8. A method according to claim 1, wherein said analyte is antibody to at least one HLA antigen, said reciprocal reagent is at least one HLA antigen, and said detecting comprises:
washing said solid support substantially free of non-specifically bound antigen;
adding a labeled moiety capable of binding to said HLA antigen; and
detecting the presence of said labeled moiety bound to said support.

9. A method according to claim 8, wherein said labeled moiety is an antibody directed against β-2 microglobulin.

10. A method according to claim 8, wherein said labeled moiety is enzyme labeled antibody directed against an HLA antigen.

11. A method according to claim 8, wherein said labeled binding moiety is fluorochrome labeled antibody directed against an HLA antigen.

12. A method for detecting the presence of antibody to at least one Class I HLA antigen in a human biological specimen, said method comprising;
combining said biological specimen with :(1) at least one Class I HLA antigen; and (2) Clq bound to a solid support;
washing said solid support substantially free of non-specifically bound antigen and antibody;

adding a labeled binding moiety comprising an antibody which binds β-2 microglobulin; and detecting by means of said labeled binding moiety the presence of immune complexes on said support as compared to a reference value;

wherein a difference in signal from said specimen as compared to said reference is indicative of the presence of said antibody to a Class I HLA antigen.

13. A method for detecting the presence of preformed immune complexes comprising at least one HLA antigen and antibody to said HLA antigen in a biological specimen, said method comprising:

combining said biological specimen with Clq bound to a solid support;

washing said solid support substantially free of non-specifically bound antigen and antibody;

adding a labeled binding moiety capable of binding to said HLA antigen;

and detecting by means of said labeled binding moiety the presence of immune complexes present on said support as compared to a reference value, wherein a difference in signal from said specimen as compared to said reference value is indicative of the presence of said immune complexes.

14. A kit for use in a method comprising:

combining said biological specimen with (1) reciprocal reagent to said analyte, wherein said reciprocal reagent is allotypic antiserum or monoclonal antibody to said analyte when said analyte is an HLA antigen and is HLA antigen when said analyte is said antibody, with the proviso that when said sample is being tested for preformed immune complexes of analyte said reagent need not be added, and (2) Clq bound to a solid support; and detecting the presence of immune complexes present on said support using a directly or indirectly labeled anti-HLA binding moiety wherein said label is capable of providing a detectable signal, said kit comprising:

a solid support coated with Clq protein;

a monoclonal antibody or allotypic antiserum reagent specific for at least one HLA antigen;

a labeled binding moiety which specifically binds to HLA.

15. A kit according to claim 14 wherein said label is an enzyme.

16. A kit according to claim 15, wherein said labeled binding moiety is an enzyme labeled antibody which specifically binds β 2-microglobulin.

17. A kit according to claim 14, wherein said labeled binding moiety is a labeled antibody which specifically binds β2-microglobulin.

* * * * *